(12) United States Patent
Bulavin et al.

(10) Patent No.: US 7,456,268 B2
(45) Date of Patent: Nov. 25, 2008

(54) MATERIALS AND METHODS FOR INHIBITING WIP1

(75) Inventors: Dmitry Bulavin, Singapore (SG); Ettore Appella, Chevy Chase, MD (US); Albert J. Fornace, Jr., Bethesda, MD (US); Anne Kallioniemi, Tampere (FI)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 11/868,794

(22) Filed: Oct. 8, 2007

(65) Prior Publication Data

US 2008/0081065 A1    Apr. 3, 2008

Related U.S. Application Data

(63) Continuation of application No. 10/507,701, filed as application No. PCT/US03/08997 on Mar. 21, 2003, now abandoned.

(60) Provisional application No. 60/366,883, filed on Mar. 22, 2002.

(51) Int. Cl.
  C07H 1/00    (2006.01)
  C07H 5/00    (2006.01)
  C07H 19/00   (2006.01)
  C07H 21/00   (2006.01)
  C07H 21/02   (2006.01)
  C08B 37/00   (2006.01)

(52) U.S. Cl. ............ 536/22.1; 536/1.11; 536/18.7; 536/23.1; 536/24.3; 536/24.31; 536/24.5

(58) Field of Classification Search ............ 536/1.11, 536/18.7, 22.1, 23.1, 24.3, 24.31, 24.5
See application file for complete search history.

(56) References Cited

U.S. PATENT DOCUMENTS 5,965,362 A    10/1999  Pinkel et al.
6,812,339 B1   11/2004  Venter et al.
2003/0032027 A1  2/2003  Li et al.
2004/0167189 A1  8/2004  Bulavin et al.

FOREIGN PATENT DOCUMENTS

WO    WO 01/55450 A2    8/2001
WO    WO 03/035843 A    5/2003
WO    WO 03/083103 A    10/2003

OTHER PUBLICATIONS

Amino acid databases. Dequence alignment between Applicants' Seq Id No. 1 and sequence 2226 from U.S. Patent 6,812,339 (filed Sep. 10, 2001).
Amino acid databases. Sequence alignment between Applicants' Seq Id No. 1 and Fiscella et al. (1997) and corresponding Accession No. U78305.
Belton, *Proceedings of the Royal Irish Academy, Section B: Biological, Geological and Chemical Science*, 74(14): 185-192 (1974).
Bulavin et al., *EMBO Journal*, 18(23): 6845-6854 (1999).
Bulavin et al., *Nature*, 411: 102-107 (2001).
Bulavin et al., *Nature Genetic*, 36(4): 343-350 (2004).
Choi et al., *Genomics*, 64: 298-306 (2000).
Fiscella et al., *Proc. Natl. Acad. Sci.*, 94: 6048-6053 (1997).
GenCore database Accession No. HSU78305, sequence alignment between Applicants' Seq Id No. 1, Seq Id No. 2 and nucleic acid database.
Kanai et al., *J. Cancer Res. Clin. Oncol.*, 127: 697-706 (2001).
Li et al., *Nature Genetics*, 31: 133-134 (Jun. 2002).
Takekawa et al., *EMBO Journal.*, 19(23): 6517-6526 (2000).
Zee-Cheng et al., *Journal of Medicinal Chemistry*, 13(2): 264-268 (1970).

*Primary Examiner*—Alana M. Harris
(74) *Attorney, Agent, or Firm*—Leydig, Voit & Mayer, Ltd.

(57) ABSTRACT

Isolated or purified oligonucleotides and isolated or purified morpholino oligomers; a method of detecting cancer or a predisposition to cancer in a mammal, comprising comparing the level of expression of Wip1 in the mammal to a control; a method of treating cancer in a mammal that expresses the same or a higher level of Wip1 as compared to a mammal of the same species that does not have cancer, comprising administering to the mammal a cancer-treating effective amount of a Wip1 inhibitor; a method of screening an oligonucleotide or morpholino oligomer for the ability to inhibit the expression of Wip1; a method of determining the efficacy with which a test oligonucleotide or morpholino oligomer inhibits Wip1 expression; a method of screening a compound for Wip1-inhibiting activity; and a method of determining the efficacy with which a test compound inhibits Wip1.

2 Claims, 1 Drawing Sheet

Figure 1

| SEQ ID NO: | NUCLEOTIDE SEQUENCE | HYBRIDIZES TO |
|---|---|---|
| 1 | CTCCCAGCGAGTACAGCCCCGCCAT | Exon 1 of Wip1 |
| 2 | CGGTCCCACGCAGCCCGCCGAATCC | 5' UTR of Wip1 |

MATERIALS AND METHODS FOR INHIBITING WIP1

This application is a continuation of U.S. patent application Ser. No. 10/507,701, filed on Oct. 14, 2004 ABN which is a 371 of PCT/US03/08997, filed Mar. 21, 2003 which claims benefit of U.S. Provisional Application Ser. No. 60/366,883 filed Mar. 22, 2002, the entire disclosure of which are hereby incorporated by reference herein in their entirety.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 735 Byte ASCII (Text) file named "701998SEQLISTING_ST25," created on Oct. 4, 2007.

FIELD OF THE INVENTION

This invention pertains to isolated or purified oligonucleotides, isolated or purified morpholino oligomers, a method of detecting cancer or a predisposition to cancer, as well as a method of treating cancer. The present invention further pertains to a method of screening an oligonucleotide or morpholino oligomer for the ability to inhibit Wip1 expression and a method of screening a compound for inhibiting Wip1 activity, in addition to a method of determining the efficacy with which an oligonucleotide or morpholino oligomer inhibits Wip1 expression and a method of determining the efficacy with which a test compound inhibits Wip1 phosphatase activity.

BACKGROUND OF THE INVENTION

Wild-type p53-induced phosphatase 1 (Wip1) is a $Mg^{2+}$-dependent serine/threonine protein phosphatase that is expressed in response to ionizing or ultra-violet (UV) radiation in a manner that is dependent on the tumor suppressor gene product p53. Its role in cancer was first suggested by Fiscella et al., *Proceedings of the National Academy of Sciences, U.S.A.* 94: 6048-6053 (1997), which reported Wip1 as an important inhibitor of growth, since ectopic expression of WIP1 (also known as PPMD1) in a human glioblastoma cell line (T98G) resulted in fewer colonies of cells. In contrast to these results, Wip1 was shown by Takekawa et al., *EMBO Journal* 19(23): 6517-6526 (2000), to dephosphorylate the kinase p38, which functions to activate p53 for the induction of apoptosis and transcription in response to environmental stress, thereby rendering Wip1 anti-apoptotic as opposed to anti-proliferative.

Consistent with Takekawa et al., Wip1 has been shown by the present inventors to be a positive regulator of tumorigenesis. WIP1, located at chromosome 17q22/q23 by FISH analysis, was found amplified in human breast tumor cell lines as well as in approximately 11% of primary breast tumors as determined by Northern blot analysis, Southern blot analysis, and tissue microarray analysis. Furthermore, exogeneous expression of WIP1 in cells expressing H-Ras-V12 resulted in a decrease in p53-mediated apoptosis and a partial rescue of these cells from cell cycle arrest. Moreover, Wip1 was demonstrated as a negative regulator of p53, since UV-induced activation of p38 kinase was significantly attenuated in breast cell lines in which the Wip1 gene was amplified and overexpressed (BT-474 and MCF7) compared to a breast line (MDA-MB436) without Wip1 amplification. Taken together, these results indicate that WIP1 is a candidate proto-oncogene involved in tumorigenesis and, thus, represents an attractive new target for cancer therapy.

In view of the foregoing, the present invention provides materials and methods for treating cancer in a mammal that expresses elevated levels of Wip1. These and other advantages of the invention, as well as additional inventive features, will be apparent from the description of the invention provided herein.

BRIEF SUMMARY OF THE INVENTION

The present invention provides an isolated or purified oligonucleotide consisting essentially of the nucleotide sequence of SEQ ID NO: 1 or SEQ ID NO: 2, as well as an isolated or purified morpholino oligomer consisting essentially of the sequence of SEQ ID NO: 1 or SEQ ID NO: 2.

The present invention further provides a method of detecting cancer or a predisposition to cancer in a mammal. The method comprises comparing the level of expression of Wip1 in a test sample comprising Wip1 obtained from the mammal to the level of expression of Wip1 in a control sample. A higher level of expression of Wip1 in the test sample as compared to the control sample is indicative of cancer or a predisposition to cancer in the mammal.

Further provided by the present invention is a method of treating cancer in a mammal that expresses the same level or a higher level of Wip1 as compared to a mammal of the same species that does not have cancer. The method comprises administering to the mammal a cancer-treating effective amount of a Wip1 inhibitor.

The present invention also provides a method of screening an oligonucleotide or morpholino oligomer for the ability to inhibit the expression of Wip1. The method comprises comparing the level of expression of Wip1 in a test sample obtained from Wip1-expressing cells that have been contacted with the oligonucleotide or morpholino oligomer to the level of expression of Wip1 in a control sample obtained from Wip1-expressing cells that have not been contacted with the oligonucleotide or morpholino oligomer. A lower level of expression of Wip1 in the test sample as compared to the control sample is indicative of the ability of the oligonucleotide or morpholino oligomer to inhibit the expression of Wip1.

A method of determining the efficacy with which a test oligonucleotide or morpholino oligomer inhibits Wip1 expression is further provided by the present invention. The method comprises comparing the level of expression of Wip1 in a test sample obtained from Wip1-expressing cells that have been contacted with the test oligonucleotide or morpholino oligomer to the level of expression of Wip1 in a control sample obtained from Wip1-expressing cells that have been contacted with an oligonucleotide or morpholino oligomer that is known to inhibit the expression of Wip1. A lower level of expression of Wip1 in the test sample as compared to the control sample is indicative of the test oligonucleotide or morpholino oligomer having a greater efficacy for inhibiting the expression of Wip1 than the known oligonucleotide or morpholino oligomer, whereas an higher level of expression of Wip1 in the test sample as compared to the control sample is indicative of the test oligonucleotide or morpholino oligomer having a lower efficacy for inhibiting the expression of Wip1 than the known oligonucleotide or morpholino oligomer.

Further provided is a method of screening a compound for Wip1-inhibiting activity. The method comprises comparing the level of Wip1 phosphatase activity in a test sample obtained from Wip1-expressing cells that have been contacted with the compound to the level of Wip1 phosphatase activity in a control sample obtained from Wip1-expressing cells that have not been contacted with the compound. A lower level of Wip1 phosphatase activity in the test sample as compared to the control sample is indicative of the ability of the compound to inhibit Wip1.

The present invention also provides a method of determining the efficacy with which a test compound inhibits Wip1. The method comprises comparing the level of Wip1 phosphatase activity in a test sample obtained from Wip1-expressing cells that have been contacted with the test compound to the level of Wip1 phosphatase activity in a control sample obtained from Wip1-expressing cells that have been contacted with a compound that is known to inhibit Wip1. A lower level of Wip1 phosphatase activity in the test sample as compared to the control sample is indicative of the test compound having a greater efficacy for inhibiting Wip1 than the known compound, whereas a higher level of Wip1 phosphatase activity in the test sample as compared to the control sample is indicative of the test compound having a lower efficacy for inhibiting Wip1 than the known compound.

BRIEF DESCRIPTION OF THE DRAWINGS

FIG. 1 represents a table of sequences (5'→3' when read from left to right) of the oligonucleotides or morpholino oligomers of the present invention and the regions to which they hybridize.

DETAILED DESCRIPTION OF THE INVENTION

The present invention provides isolated or purified oligonucleotides consisting essentially of the nucleotide sequence of SEQ ID NO: 1 or SEQ ID NO: 2, which can be used in the methods described herein. The term "isolated" as used herein means having been removed from its natural environment. The term "purified" as used herein means having been increased in purity, wherein "purity" is a relative term, and not to be construed as absolute purity. The term "oligonucleotide" as used herein means a polymer of DNA or RNA, (i.e., a polynucleotide), which can be single-stranded or double-stranded, synthesized or obtained from natural sources, and which can contain natural, non-natural or altered nucleotides. With respect to the isolated or purified oligonucleotide of the present invention, it is preferred that no insertions, deletions, inversions, and/or substitutions are present in the oligonucleotide. However, it may be suitable in some instances for the isolated or purified oligonucleotide of the present invention to comprise one or more insertions, deletions, inversions, and/or substitutions. It is, furthermore, preferred that the isolated or purified oligonucleotides of the present invention are synthesized, single-stranded polymers of DNA.

Isolated or purified morpholino oligomers consisting essentially of the sequence of SEQ ID NO: 1 or SEQ ID NO: 2 are further provided by the present invention. The term "morpholino oligomer" as used herein refers to a polymer of the genetic nitrogeneous bases, adenine, guanine, cytosine, and thymine, in which the nitrogenous bases are linked to a 6-membered morpholine ring, as opposed to ribose or deoxyribose as in RNA or DNA. Also, each unit of the morpholino oligomer that comprises the nitrogeneous base and the morpholine ring is bridged to neighboring units via phosphorodiamidate linkages, in contrast to the phosphodiester linkages of oligonucleotides. For more description of morpholino oligomers, see Summerton et al., *Antisense & Nucleic Acid Drug Development* 7:187-195 (1997).

The sequence of the nitrogeneous bases of the morpholino oligomers is essential for their use in the methods described herein. Like the oligonucleotides of the present invention, it is preferred that the morpholino oligomers do not comprise any insertions, deletions, inversions, and/or substitutions. However, it may be suitable in some instances for one or more insertions, deletions, inversions, and/or substitutions to be present in the morpholino oligomers of the present invention. It is, furthermore, preferred that the isolated or purified morpholino oligomers of the present invention are single-stranded.

A variety of techniques used to synthesize the oligonucleotides of the present invention are known in the art. See, for example, Lemaitre et al., *Proceedings of the National Academy of the Sciences* 84: 648-652 (1987). Likewise, a variety of techniques employed for the synthesis of morpholino oligomers are known in the art. See, for example, U.S. Pat. No. 5,185,444. Alternatively, the oligonucleotides or morpholino oligomers of the present invention can be purchased from companies, such as Eurogentec, Belgium (for oligonucleotides) and Gene Tools, Philomath, Oreg. (for morpholino oligomers).

The present invention further provides a method of detecting cancer or a predisposition to cancer in a mammal. The method comprises comparing the level of expression of Wip1 in a test sample comprising Wip1 obtained from the mammal to the level of expression of Wip1 in a control sample, wherein the control sample is a sample comprising Wip1 taken from a mammal, desirably of the same species, which is known to not have cancer or a predisposition to cancer. In this method, a higher level of expression of Wip1 in the test sample as compared to the control sample is indicative of cancer or a predisposition to cancer in the mammal.

With respect to the above method, in addition to the other methods of the present invention, wherein the method comprises comparing the level of expression of Wip1, a variety of techniques known in the art can be used to compare the level of expression of Wip1. For example, Western blotting can be used to compare the levels of Wip1 protein expressed in two different cell populations. Alternatively, Northern blotting can be used to compare the levels of Wip1 mRNA expressed in two different cell populations. Finally, Southern blotting can be used to compare the number of copies of the Wip1 gene found in two different cell populations. These processes are described in Sambrook et al., *Molecular Cloning: A Laboratory Manual*, $2^{nd}$ Ed., Cold Spring Harbor Press, Cold Spring Harbor, N.Y. (1989).

For purposes of the present invention, mammals include, but are not limited to, the order Rodentia, such as mice, and the order Logomorpha, such as rabbits. It is preferred that the mammals are from the order Carnivora, including Felines (cats) and Canines (dogs). It is more preferred that the mammals are from the order Artiodactyla, including Bovines (cows) and Suines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

In a preferred embodiment of the present inventive method of detecting cancer or a predisposition to cancer, Wip1 is in the form of nucleic acid in the test sample and the control sample. The term "nucleic acid" as used herein refers to a chain of nucleotides, as in DNA and RNA. In another preferred embodiment of the present inventive method, Wip1 is in the form of protein in the test sample and the control sample.

The present invention also provides a method of treating cancer in a mammal that expresses the same level or a higher level of Wip1 as compared to a mammal of the same species that does not have cancer. The method comprises administering to the mammal a cancer-treating effective amount of a Wip1 inhibitor. A "cancer-treating effective amount" of a Wip1 inhibitor is an amount sufficient to inhibit the progression of cancer to any degree. It is understood by one of ordinary skill in the art that the inhibition mediated by an inhibitor does not require complete inhibition, as a beneficial or therapeutic effect can be realized with any degree of inhibition. Rather, there are varying degrees of inhibition. In this regard, any suitable inhibitor of Wip1 can be used.

With respect to the present inventive methods, wherein cancer or a predisposition to cancer is either detected or treated, the cancer can be cancer of any tissue from a mammal. Preferably, the cancer is cancer of the breast.

In a preferred embodiment of the above inventive method, the Wip1 inhibitor is an oligonucleotide or a morpholino oligomer that inhibits Wip1 by preventing the expression of either Wip1 mRNA or Wip1 protein, such as by hybridizing to any part of a nucleic acid encoding (i.e., DNA or RNA) Wip1. The oligonucleotide or morpholino oligomer for use in the present inventive method desirably comprises any sequence that is substantially complementary to the sequence of the untranslated region (UTR) of a nucleic acid encoding Wip1 or is substantially complementary to the sequence of a nucleic acid encoding Wip1, such that the oligonucleotide or morpholino oligomer selectively hybridizes to the Wip1 gene or Wip1 mRNA, thereby inhibiting transcription of the gene or translation of the mRNA. It is desirable for the selective hybridization to be highly stringent. In other words, the oligonucleotides or morpholino oligomers specifically hybridize to target sequences of Wip1 mRNA or the Wip1 gene in an amount that is detectably stronger than non-specific hybridization.

Preferably, the oligonucleotide or morpholino oligomer comprises at least 18 genetic nitrogenous bases. More preferably, the oligonucleotide or morpholino oligomer comprises 25 genetic nitrogenous bases. Preferably, the oligonucleotide or morpholino oligomer hybridizes to exon 1 of a nucleic acid encoding Wip1. In an even more preferred embodiment of the present invention, the oligonucleotide or morpholino oligomer comprises the sequence 5'-CTC-CCAGCGAGTACAGCCCCGCCAT-3' (SEQ ID NO: 1). Alternatively and also preferably, the oligonucleotide or morpholino oligomer hybridizes to any part of an UTR of a nucleic acid encoding Wip1. The oligonucleotide or morpholino oligomer of the present invention can hybridize to any part of the 3' UTR, which is the region located downstream of the stop codon of the nucleic acid encoding Wip1. Alternatively, the oligonucleotide or morpholino oligomer hybridizes to the 5' UTR, which is the region located upstream of the initiation codon of the nucleic acid encoding Wip1. In this instance, it is most preferred that the oligonucleotide or morpholino oligomer comprises the sequence 5'-CG-GTCCCACGCAGCCCGCCGAATCC-3' (SEQ ID NO: 2).

The oligonucleotide can comprise at least one modified oligodeoxynucleotide. For example, the oligonucleotide can contain at least one variant linkage that bridges one nucleotide to another, such as a phosphoroamidate linkage or a phosphorothioate linkage instead of the phosphodiester linkages found in unmodified oligonucleotides.

The inhibitor alternatively can be a compound that inhibits Wip1 phosphatase activity. It is to be understood that the inhibition of Wip1 phosphatase activity does not require complete inhibition, as a beneficial or therapeutic effect can be realized with any degree of inhibition. Rather, there are varying degrees of inhibition. The compound that inhibits Wip1 phosphatase activity can be a small molecular weight compound. As used herein, the term "small molecular weight compound" refers to a compound having a molecular weight of less than about 10 kDa as measured by, for example, gel filtration chromatography. One skilled in the art will appreciate that a small molecular weight compound is, generally, a non-peptidic compound that is cell permeable and resistant to degradation. The term "non-peptidic" as used herein refers to not being derived from a protein.

The Wip1 inhibitor can be administered in a variety of forms. For example, when the Wip1 inhibitor is an oligonucleotide or morpholino oligomer, the oligonucleotide or morpholino oligomer can be administered in the form of a liposome. Alternatively, the oligonucleotide or morpholino oligomer can be administered in the form of a vector. One of ordinary skill in the art will appreciate that any of a number of vectors known in the art are suitable for use in the invention. Examples of suitable vectors include, for instance, plasmids, plasmid-liposome complexes, and viral vectors, e.g., parvoviral-based vectors (i.e., adeno-associated virus (AAV)-based vectors), retroviral vectors, herpes simplex virus (HSV)-based vectors, and adenovirus-based vectors. Any of these expression constructs can be prepared using standard recombinant DNA techniques described in, e.g., Sambrook et al. (1989), supra and Ausubel et al., Current Protocols in Molecular Biology, Greene Publishing Associates and John Wiley & Sons, New York, N.Y. (1994).

In addition, the Wip1 inhibitor can be administered with a carrier. The carrier can be any suitable carrier. Preferably, the carrier is pharmaceutically acceptable. With respect to the oligonucleotides or morpholino oligomers of the present invention, the carrier can be any of those conventionally used and is limited only by chemico-physical considerations, such as solubility and lack of reactivity with the oligonucleotides or morpholino oligomers of the present invention, and by the route of administration. The pharmaceutically acceptable carriers described herein, for example, vehicles, adjuvants, excipients, and diluents, are well-known to those skilled in the art and are readily available to the public. Typically, the pharmaceutical composition comprising the carrier and the oligonucleotide or morpholino oligomer can comprise a physiological saline solution; dextrose or other saccharide solution; or ethylene, propylene, polyethylene, or other glycol. It is preferred that the pharmaceutically acceptable carrier be one which is chemically inert to the oligonucleotides or morpholino oligomers and one which has no detrimental side effects or toxicity under the conditions of use. The choice of carrier will be determined, in part, by the particular Wip1 inhibitor and by the particular method used to administer the resulting composition. Preferably, the oligonucleotides or morpholino oligomers are administered with the carrier ethoxylated polyethylenimine (EPEI), which is a weakly basic delivery reagent that electrostatically binds to the anionic charges of oligonucleotides and morpholino/oligonucleotide duplexes. See Morcos, *Genesis* 30: 94-102 (2001), for more description on this method.

One skilled in the art will appreciate that suitable methods of administering a Wip1 inhibitor, such as an oligonucleotide or a morpholino oligomer of the present invention, to a mammal, such as a human, are known, and, although more than one route can be used to administer a particular composition, a particular route can provide a more immediate and more effective reaction than another route. If the cancer is in the form of a tumor, preferably the Wip1 inhibitor is administered peritumorally or intratumorally.

Formulations suitable for oral administration can consist of (a) liquid solutions, such as an effective amount of the oligonucleotide or morpholino oligomer dissolved in diluents, such as water or saline, (b) capsules, sachets or tablets, each containing a predetermined amount of the active ingredient, as solids or granules, (c) suspensions in an appropriate liquid, and (d) suitable emulsions.

Tablet forms can include one or more of lactose, mannitol, cornstarch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, such carriers as are known in the art.

Formulations suitable for parenteral administration include aqueous and non-aqueous solutions, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The Wip1 inhibitor, such as the oligonucleotides or morpholino oligomers of the present invention, can be administered alone or in combination with other suitable components. Such components include other active agents, such as anticancer agents and agents that help the Wip1 inhibitor inhibit expression of Wip1 protein or Wip1 mRNA or Wip1 phosphatase activity more effectively.

The amount or dose of the Wip1 inhibitor administered to a mammal, particularly a human, in the context of the present invention should be sufficient to effect a therapeutic response in the animal over a reasonable time frame. The dose will be determined by the efficacy of the particular Wip1 inhibitor and the condition of the animal (e.g., human), as well as the body weight of the animal (e.g., human) to be treated. The size of the dose also will be determined by the existence, nature and extent of any adverse side effects that might accompany the administration of a particular Wip1 inhibitor. Ultimately, the attending physician will decide the dosage of the Wip1 inhibitor of the present invention with which to treat each individual patient, taking into consideration a variety of factors, such as age, body weight, general health, diet, sex, inhibitor to be administered, route of administration, and the severity of the cancer being treated.

A method of screening an oligonucleotide or morpholino oligomer for the ability to inhibit the expression of Wip1 is further provided by the present invention. The method comprises comparing the level of expression of Wip1 in a test sample obtained from Wip1-expressing cells that have been contacted with the oligonucleotide or morpholino oligomer to the level of expression of Wip1 in a control sample obtained from Wip1-expressing cells that have not been contacted with the oligonucleotide or morpholino oligomer. In this method, a lower level of expression of Wip1 in the test sample as compared to the control sample is indicative of the ability of the oligonucleotide or morpholino oligomer to inhibit the expression of Wip1.

Further provided by the present invention is a method of determining the efficacy with which a test oligonucleotide or morpholino oligomer inhibits Wip1 expression. The method comprises comparing the level of expression of Wip1 in a test sample obtained from Wip1-expressing cells that have been contacted with the test oligonucleotide or morpholino oligomer to the level of expression of Wip1 in a control sample obtained from Wip1-expressing cells that have been contacted with an oligonucleotide or morpholino oligomer that is known to inhibit the expression of Wip1. A lower level of expression of Wip1 in the test sample as compared to the control sample is indicative of the test oligonucleotide or morpholino oligomer having a greater efficacy for inhibiting the expression of Wip1 than the known oligonucleotide or morpholino oligomer, whereas a higher level of expression of Wip1 in the test sample as compared to the control sample is indicative of the test oligonucleotide or morpholino oligomer having a lower efficacy for inhibiting the expression of Wip1 than the known oligonucleotide or morpholino oligomer.

Wip1 can be in the form of nucleic acid in the test sample and the control sample. Alternatively, Wip1 can be in the form of protein in the test sample and the control sample.

With respect to the method of screening an oligonucleotide or morpholino oligomer and the method of determining the efficacy with which a test oligonucleotide or morpholino oligomer inhibits Wip1 expression, a variety of techniques known in the art can be used to compare the level of expression of Wip1. For example, Western blotting can be used to compare the levels of Wip1 protein expressed in two different cell populations. Alternatively, Northern blotting can be used to compare the levels of Wip1 mRNA expressed in two different cell populations. Finally, Southern blotting can be used to compare the number of copies of the Wip1 gene found in two different cell populations. These processes are described in Sambrook et al. (1989), supra.

The present invention also provides a method of screening a compound for Wip1-inhibiting activity. The method comprises comparing the level of Wip1 phosphatase activity in a test sample obtained from Wip1-expressing cells that have been contacted with the compound to the level of Wip1 phosphatase activity in a control sample obtained from Wip1-expressing cells that have not been contacted with the compound. A lower level of Wip1 phosphatase activity in the test sample as compared to the control sample is indicative of the ability of the compound to inhibit Wip1.

A method of determining the efficacy with which a test compound inhibits Wip1 is also provided by the present invention. The method comprises comparing the level of Wip1 phosphatase activity in a test sample obtained from Wip1-expressing cells that have been contacted with the test compound to the level of Wip1 phosphatase activity in a control sample obtained from Wip1-expressing cells that have been contacted with a compound that is known to inhibit Wip1. In this method, a lower level of Wip1 phosphatase activity in the test sample as compared to the control sample is indicative of the test compound having a greater efficacy for inhibiting Wip1 than the known compound, whereas a higher level of Wip1 phosphatase activity in the test sample as compared to the control sample is indicative of the test compound having a lower efficacy for inhibiting Wip1 than the known compound.

A variety of techniques known in the art can be used to compare levels of phosphatase activity. An example of a Wip1 phosphatase activity assay can be found in Fiscella et al. (1997), supra.

The following examples further illustrate the invention but, of course, should not be construed as in any way limiting its scope.

EXAMPLES

Abbreviations

For convenience, the following abbreviations are used herein: Wip1, wild-type p53-induced phosphatase; UV, ultraviolet; PPMD1, protein phosphatase, magnesium-dependent 1; FISH, fluorescent in situ hybridization; mRNA, messenger RNA; UTR, untranslated region; HSV, herpes simplex virus; AAV, adeno-associated virus; EPEI, ethoxylated polyethylenimine; GAPDH, glyceraldehyde 3-phosphate dehydrogenase; GADD34, growth arrest and DNA damage-inducible 34; and PCR, polymerase chain reaction; cDNA, complementary DNA; BAC, bacteria artificial chromosome; dUTP, deoxyuridine triphosphate; MEF, mouse embryo fibroblasts.

The following references, to the extent that they provide exemplary procedural or other details supplementary to those set forth herein, are specifically incorporated herein by reference:

Birren et al., *Genome Analysis: A Laboratory Manual Series, Volume 1, Analyzing DNA*, Cold Spring Harbor Laboratory Press, Cold Spring Harbor, N.Y. (1997), Birren et al., *Genome Analysis: A Laboratory Manual Series, Volume 2, Detecting Genes*, Cold Spring Harbor Laboratory Press, Cold Spring Harbor, N.Y. (1998), Birren et al., *Genome Analysis: A Laboratory Manual Series, Volume 3, Cloning Systems*, Cold Spring Harbor Laboratory Press, Cold Spring Harbor, N.Y. (1999), Birren et al., *Genome Analysis: A Laboratory Manual Series, Volume 4, Mapping Genomes*, Cold Spring Harbor Laboratory Press, Cold Spring Harbor, N.Y. (1999), Harlow et al., *Antibodies: A Laboratory Manual*, Cold Spring Harbor Laboratory Press, Cold Spring Harbor, N.Y. (1988), Harlow et al., *Using Antibodies: A Laboratory Manual*, Cold Spring Harbor Laboratory Press, Cold Spring Harbor, N.Y. (1999), Hoffman, *Cancer and the Search for Selective Biochemical Inhibitors*, CRC Press (1999), Pratt, *The Anticancer Drugs*, 2nd edition, Oxford University Press, NY (1994),

*QIAexpress Detection and Assay Handbook*, 2nd edition, QIAGEN Inc., 28159 Avenue Stanford, Valencia, Calif. 91355 (April 1999), and Sambrook et al. (1989), supra.

Example 1

This example demonstrates the expression levels of Wip1 mRNA in human tumor cell lines and tumor samples.

Total RNA was extracted from 67 human tumor cell lines of which 58 are listed in O'Connor et al., *Cancer Research* 57: 4285-4300 (1997) and 11 are IMR-90, NDA-N, Sum 52, NCI-ADR, BT-474, MCF7, MCI-H %22, ACHN, CAKI-1, MOLT4, and OVCAR4, in addition to 11 tumor samples (National Cancer Institute, National Institutes of Health), using the RNeasy kit (Qiagen, Inc., Valencia, Calif.). Wip1 mRNA levels in primary breast tumors were determined after reverse transcription coupled to the Real-Time PCR procedure using an ABI PRISM® 7700 Sequence Detection System (Applied Biosystems, Foster City, Calif.) and the SYBR Green PCR Master Mix (Applied Biosystems, Foster City, Calif.). Expression levels were determined relative to the expression of GAPDH and GADD34. The following primers were used: WIP1: 5'-tgcccgggagcacttgt-3'/5'-ggcagcgcaaac-cttagc-3' and 5'-gacccgaaggatgactttgtc-3'/5'-gcttctgagggtcaa-gagtg-3'; GADD34, 5'-cctctacttctgccttgtctcca-3'/5'-ccgtggct-tgattctcttcct-3'; and GAPDH, 5-gaaggtgaaggtcggagtc-3'/5'-gaagatggtgatgggatttc-3'. mRNA levels in the panel of human tumor cell lines were analyzed using a dot-blotting procedure described in Koch-Paiz et al., *Biotechniques* 29: 706-714 (2000). polyU served as a control for relative mRNA content.

In the human tumor cell lines tested, Wip1 mRNA levels were 4.7 to 9.4 times higher in the four breast tumor cell lines MDA-MB361, BT474, MCF-7 and KPL-1 as compared to IMR-90 cells. This analysis demonstrated that Wip1 mRNA was overexpressed in tumor samples.

Example 2

This example demonstrates that WIP1 is amplified in some breast cancer cell lines.

Genomic DNA from IMR-90, NDA-N, Sum52, NCI-ADR, BT-474, MCF7, MCI-H %22, ACHN, CAKI-1, MOLT4, and OVCAR4 cell lines were digested with PvuII enzyme (New England Biolabs, Beverly, Mass.) The digested DNA was Southern blotted according to Sambrook et al. (1989), supra, using probes comprising the full-length cDNA sequence of Wip1, which has the GenBank accession number, U78305. From this analysis, it was shown that MCF7 and BT-474 breast cancer cell lines, and not the other cell lines tested, overexpressed WIP1. This analysis demonstrated that Wip1 mRNA was overexpressed in breast cancer.

Example 3

This example demonstrates the amplification of WIP1 in primary tumors.

The BLASTN program (http://www.ncbi.nlm.nih.gov/BLAST/) was used to localize the WIP1 gene to three overlapping bacteria artificial chromosome (BAC) clones (RP11-15E18, RP11-634F5, and RP11-1081E4) in the draft human genome sequence that map to 17q23 (http://www.ncbi.nlm.nih.gov/genome/guide/human/). BAC clone RP11-634F5, representing WIP1, labeled with SpectrumOrange-deoxyuridine triphosphate (dUTP) (Applied Biosystems, Foster City, Calif.) and centromere specific, SpectrumGreen-dUTP-labeled chromosome 17 probe (Applied Biosystems, Foster City, Calif.) were hybridized to a tissue microarray containing primary breast tumors (Kononen et al., *Nature Medicine* 4: 844-847 (1998)). Nuclei were stained with 4',6-diamidino-2-phenylindole (Sigma-Aldrich, St. Louis, Mo.). Tumor samples with at least a 3-fold increase in the number of WIP1 signals, as compared with chromosome 17 centromere signals, were considered to be amplified. Accordingly, 37 of the 326 (11.3%) tumors tested had WIP1 region amplified. From this example, it is evident that the WIP1 is amplified in some primary tumors.

Example 4

This example demonstrates the effect of WIP1 overexpression, on p38-mediated phosphorylation of p53.

IMR-90 cells were infected with plasmids encoding Wip1, which were made by cloning the Wip1 cDNA into the PINCO vector (Grignani, et al., *Cancer Research* 58: 14-19 (1998)) using BamHI/NotI sites, and with H-RasV12, which was obtained from S. Lowe (Cold Spring Harbor Laboratory, Cold Spring Harbor, N.Y.). p53 was immunoprecipitated from 1 mg of the total protein extract from these cells and phosphorylation on Ser33 or Ser46 of p53 was assessed by Western blotting with antibodies specific for phosphorylated p53 as described in Sakaguchi et al., *Genes Development* 12: 2831-2841 (1998). In cells that overexpressed Wip1, p53 had little, if any, phosphorylation on Ser 33 or Ser46 as compared to cells infected with H-RasV12 alone. From this example, it is evident that the overexpression of WIP1 results in less phosphorylation of p53 on sites phosphorylated by p38 kinase.

Example 5

This example demonstrates that WIP1 phosphatase complements different oncogene proteins for growth in soft agar.

Retroviruses containing WIP1 and different oncogenes, including H-RasV12, MYC or NEU1, were co-infected into wild-type mouse embryo fibroblasts (MEFs) and were analyzed for anchorage-independent growth and the ability to form foci in soft agar. The IRES c-myc (human) retroviral vector, pBabeMNIRESgfpmyc, (Oster et al., *Molecular and Cellular Biology* 20: 6768-6778 (2000)) was kindly provided by L. Z. Penn (Toronto University, Toronto, Ontario); pBabe-c-neu (Bargmann et al., *Cell* 45: 649-657 (1986)) (rat) was obtained from P. Sicinski (Dana-Farber Cancer Institute, Boston, Mass.). Suppression of colony formation was determined 2-3 weeks after infection of MEFs in 100 mm dishes with the designated retroviruses. Colonies were selected with 500 µg/ml G418 (Sigma-Aldrich, St. Louis, Mo.), and fixed and stained with 0.1% crystal violet (Sigma-Aldrich, St. Louis, Mo.). For soft agar cloning, 20,000 puromycin-(Sigma-Aldrich, St. Louis, Mo.) selected, infected cells were seeded in 0.5% agar into each well of 6-well plates. Samples were analyzed in triplicate. The results of this assay are shown below in Table 1.

TABLE 1

| MEF type | Retrovirus | Growth in soft agar |
| --- | --- | --- |
| Wild-type | Puro | − |
|  | H-rasV12 | − |
|  | neu | − |
|  | myc | − |
|  | Wip1 | − |
|  | H-rasV12 + Wip1 | + |
|  | neu + Wip1 | + |
|  | myc + Wip1 | + |
|  | ras + myc | ++ |
|  | ras + neu | + |
| p53−/− | Puro | − |
|  | H-rasV12 | ++ |
|  | Wip1 | − |
|  | H-rasV12 + Wip1 | ++ |
|  | Neu | +++ |
|  | myc | +++ |

Score: + = 10-30 colonies; ++ = 30-100 colonies; +++ = more than 100 colonies per well of a 6-well plate.

In both assays, WIP1 complemented H-RasV12 for transformation of wild-type MEFs. From this analysis, it became evident that WIP1 is a proto-oncogene.

Example 6

This example demonstrates a method of delivering morpholino oligomers to cells in culture.

Morpholino oligomers comprising the sequence of SEQ ID NO: 1 or SEQ ID NO: 2 were synthesized by and purchased from Gene Tools (Philomath, Oreg.). Sterile water (600 microliters (µl)) was added to one vial containing 300 nM of Special Delivery morpholino/DNA (Gene Tools, Philomath, Oreg.) to make a 0.5 millimolar (MM) stock solution. Sterile water (200 µl) was added to 100 nM Special Delivery Standard Control morpholino oligomers (Gene Tools, Philomath, Oreg.) to make a 0.5 stock solution. In a 15 mililiter (ml) centrifuge tube, sterile water (188.8 µl) was mixed with 5.6 µl of the 0.5 mM Special Delivery morpholino oligomer/DNA stock solution and 5.6 µl 200 micromolar (µM) EPEI Special Delivery solution (Gene Tools, Philomath, Oreg.) and vortexed immediately upon mixing. The mixture was then incubated at room temperature for exactly 20 minutes. Serum-free medium (1.8 ml) was added to the mixture and vortexed immediately upon addition. This mixture (500 µl) was then added to media-free cells and incubated in an incubator for 3 hours. Afterwards, the mixture was removed from the cells via centrifugation and fresh media containing serum was added to the cells. The cells were then incubated for at least 16 hours before testing for delivery of the morpholino oligomers. This example demonstrates a method of delivering morpholino oligomers to cultured cells.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An isolated or purified oligonucleotide consisting essentially of the nucleotide sequence of SEQ ID NO: 1.

2. An isolated or purified morpholino oligomer consisting essentially of the sequence of SEQ ID NO: 1.

* * * * *

```
                              SEQUENCE LISTING

<160> NUMBER OF SEQ ID NOS: 2

<210> SEQ ID NO 1
<211> LENGTH: 25
<212> TYPE: DNA
<213> ORGANISM: Artificial
<220> FEATURE:
<223> OTHER INFORMATION: Synthetic

<400> SEQUENCE: 1
ctcccagcga gtacagcccc gccat                                            25

<210> SEQ ID NO 2
<211> LENGTH: 25
<212> TYPE: DNA
<213> ORGANISM: Artificial
<220> FEATURE:
<223> OTHER INFORMATION: Synthetic

<400> SEQUENCE: 2
cggtcccacg cagcccgccg aatcc                                            25
```